United States Patent
Torre et al.

(10) Patent No.: US 9,528,164 B2
(45) Date of Patent: Dec. 27, 2016

(54) SUGAR RECOVERY METHOD FROM LIGNO-CELLULOSIC BIOMASS

(71) Applicant: BETA RENEWABLES S.P.A., Tortona (IT)

(72) Inventors: Paolo Torre, Arenzano (IT); Simone Ferrero, Tortona (IT); Piero Ottonello, Milan (IT); Liliane Tonet Rensi, Tortona (IT); Francesco Cherchi, Novi Ligure (IT); Dario Giordano, Tortona (IT)

(73) Assignee: Beta Renewables S.p.A., Tortona (AL) (IT)

( * ) Notice: Subject to any disclaimer, the term of this patent is extended or adjusted under 35 U.S.C. 154(b) by 246 days.

(21) Appl. No.: 14/368,572

(22) PCT Filed: Jan. 9, 2013

(86) PCT No.: PCT/IB2013/050186
§ 371 (c)(1),
(2) Date: Jun. 25, 2014

(87) PCT Pub. No.: WO2013/105033
PCT Pub. Date: Jul. 18, 2013

(65) Prior Publication Data
US 2015/0136120 A1     May 21, 2015

(30) Foreign Application Priority Data
Jan. 9, 2012   (IT) .............................. TO2012A0007

(51) Int. Cl.
C13K 1/02     (2006.01)
C12P 19/02    (2006.01)
C12P 19/14    (2006.01)
C13K 1/04     (2006.01)
C13K 13/00    (2006.01)

(52) U.S. Cl.
CPC ................ C13K 1/02 (2013.01); C12P 19/02 (2013.01); C12P 19/14 (2013.01); C13K 1/04 (2013.01); C13K 13/002 (2013.01)

(58) Field of Classification Search
None
See application file for complete search history.

(56) References Cited

U.S. PATENT DOCUMENTS 4,594,322 A    6/1986   Thompson et al.
9,234,224 B2 *  1/2016   Garbero ................ C12P 19/02

OTHER PUBLICATIONS

Xiao et al., Effects of Sugar Inhibition on Cellulases and B-Glucosidase During Enzymatic Hydrolysis of Softwood Substrates, Forest Products Biotechnology, 2004, pp. 1115-1126, Humana Press Inc.
(Continued)

Primary Examiner — Melvin C Mayes
Assistant Examiner — Stefanie Cohen
(74) Attorney, Agent, or Firm — Edwin A. Sisson, Attorney at Law, LLC; Jeffrey J. Banyas

(57) ABSTRACT

Disclosed in this specification is a process for the improved hydrolysis of glucans to glucose wherein a portion of the glucose is removed from the process to improve the yield of glucose.

26 Claims, 7 Drawing Sheets

(56) References Cited

OTHER PUBLICATIONS

Andric et al., Reactor design for minimizing product inhibition during enzymatic lignocellulose hydrolysis II. Quantification of inhibition and suitability of membrane reactors, Biotechnology Advances, 2010, pp. 407-425, Elsevier Inc.

Andric et al., Reactor design for minimizing product inhibition during enzymatic lignocellulose hydrolysis: I. Significance and mechanism of cellobiose and glucose inhibition on cellulolytic enzymes, Biotechnology Advances, 2010, pp. 308-324, Elsevier Inc.

Andric et al., Effect and Modeling of Glucose Inhibition and in Situ Glucose Removal During Enzymatic Hydrolysis of Pretreated Wheat Straw, Appl Biochem Biotechnol, Jan. 23, 2009, pp. 280-297, vol. 160, Humana Press Inc.

Elander et al., Summary of findings from the Biomass Refining Consortium for Applied Fundamentals and Innovation (CAFI): corn stover pretreatment, Cellulose, Jun. 26, 2009, pp. 649-659, vol. 16, Springer Science+Business Media B.V.

Qing et al., Hydrolysis of different chain length xylooliogmers by cellulase and hemicellulase, Bioresource Technology, Sep. 6, 2010, pp. 1359-1366, vol. 102, Elsevier Ltd.

Shi et al., Application of cellulase and hemicellulase to pure xylan, pure cellulose, and switchgrass solids from leading pretreatments, Bioresource Technology, Apr. 8, 2011, pp. 11080-11088, vol. 102, Elsevier Ltd.

Kumar et al., Effect of Enzyme Supplementation at Moderate Cellulase Loadings on Initial Glucose and Xylose Release from Corn Stover Solids Pretreated by Leading Technologies, Biotechnology and Bioengineering, Jul. 25, 2008, pp. 457-467, Wiley Periodicals, Inc.

Kim et al., Pretreatment of Corn Stover by Low-Liquid Ammonia Recycle Percolation Process, Applied Biochemistry and Biotechnology, 2006, pp. 41-57, vol. 133, Humana Press Inc.

\* cited by examiner

SUGAR RECOVERY METHOD FROM LIGNO-CELLULOSIC BIOMASS

PRIORITY AND CROSS REFERENCES

This patent application claims the priority from International Application PCT/IB2013/050186 filed on 9 Jan. 2013 and Italian Patent Application TO2012A000007 filed on 9 Jan. 2012 the teachings of both of which are incorporated in their entirety.

SUMMARY

This specification discloses a process for the improved hydrolysis based upon the principle of removing the glucose during the hydrolysis reaction so as to improve the overall glucose yield.

Disclosed in this specification is an improved process for the hydrolysis of a pre-treated ligno-cellulosic biomass comprising a solid stream and a liquid stream, said solid stream comprising glucans, xylans and compounds that are not glucans or xylans, said liquid stream comprising xylooligomers, water and compounds which are not xylooligomers.

The process comprises the steps of:
a) mixing the solid stream and a first portion of the liquid stream;
b) hydrolyzing in a first hydrolysis step at least a portion of the glucans in the solid stream to glucose and at least a portion of the xylooligomers in the first portion of the liquid stream to xylose in the presence of a first hydrolysis catalyst to create a first hydrolysis mixture having a first hydrolysis mixture monomeric sugars concentration and a first hydrolysis mixture hydrolysis catalyst concentration, wherein the first hydrolysis mixture has a first hydrolysis mixture catalyst to monomeric sugars ratio which is the ratio of the weight of the hydrolysis catalyst in the first hydrolysis mixture to the total weight of monomeric sugars in the first hydrolysis mixture;
and
c) removing at least a portion of the monomeric sugars from the first hydrolysis mixture to create:
  i) a first product stream comprising water, glucose and xylose, wherein said first product stream has a first product stream monomeric sugars concentration, a first product stream catalyst concentration which could be 0 and a first product stream catalyst to monomeric sugars ratio which is the ratio of first product stream catalyst concentration to the first product stream monomeric sugars concentration and
  ii) a partly hydrolyzed stream, which is the first hydrolysis mixture which has had at least a portion of the monomeric sugars removed,
wherein the removal of at least a portion of the monomeric sugars from the first hydrolysis mixture occurs while the hydrolysis of at least a portion of the glucans to glucose is still being conducted
and
the first hydrolysis mixture catalyst to monomeric sugars ratio is greater than or equal to the first product stream catalyst to monomeric sugars ratio.

It is also disclosed that the process may further comprise the steps of:
a) mixing the partly hydrolyzed stream and a second portion of the liquid stream;
b) hydrolyzing in a second hydrolysis step at least a portion of the glucans in the partly hydrolyzed stream to glucose and at least a portion of the xylooligomers in the second portion of the liquid stream to xylose in the presence of a second hydrolysis catalyst comprising at least a portion of the first hydrolysis catalyst to create a second hydrolysis mixture, and
c) removing at least a portion of the monomeric sugars from the second hydrolysis mixture to create a second monomeric sugars product stream comprising water, glucose and xylose.

It is further disclosed that the first hydrolysis may occurs in a first vessel, and that the second hydrolysis step may occur in a second vessel.

It is also disclosed that the first hydrolysis step and the second hydrolysis step may occur in the same vessel.

It is further disclosed that the removal of the monomeric sugars from the first hydrolysis mixture and/or the second hydrolysis mixture may occur outside the first vessel.

It is also disclosed that at least a portion of the partly hydrolyzed stream may be purged from the process.

It is further disclosed that at least a portion of the first hydrolysis mixture and/or the second hydrolysis mixture may be purged from the process.

It is also disclosed that at least a portion of the glucans, xylans, and compounds which are not glucans or xylans may be purged from the process.

It is further disclosed that the partly hydrolyzed stream may has a partly hydrolyzed stream monomeric sugars concentration, and ratio of the partly hydrolyzed stream monomeric sugars concentration to the first hydrolysis mixture monomeric sugars concentration may be less than or equal to 1.0.

It is also disclosed that the hydrolysis may comprise enzymatic hydrolysis and the catalyst comprise at least one enzyme capable of hydrolyzing glucans to glucose.

It is further disclosed that the removal of at least a portion of the monomeric sugars from the first hydrolysis mixture and/or the second hydrolysis mixture may be comprised of a process selected from the group consisting of centrifugation, filtration and a combination thereof.

It is also disclosed that the removal of at least a portion of the monomeric sugars from the first hydrolysis mixture and/or the second hydrolysis mixture may comprise nanofiltration.

It is further disclosed that the removal of at least a portion of the monomeric sugars from the first hydrolysis mixture and/or the second hydrolysis mixture may comprise ultrafiltration.

It is also disclosed that the removal of at least a portion of the monomeric sugars from the first hydrolysis mixture and/or the second hydrolysis mixture may comprise centrifugation.

It is further disclosed that the ratio of the mass of the material purged from the process to the mass of the partly hydrolyzed stream introduced into the first vessel or the second vessel may be in a range selected from the group of ranges consisting of 1:99 to 99:1, 5:95 to 50:50, 50:50 to 95:5, 10:90 to 90:10, 20:80 to 80:20, 30:70 to 70:30, and 40:60 to 60:40.

It is also disclosed that the ratio on a dry basis of the amount of the pre-treated ligno-cellulosic biomass added to the process to the amount of the first hydrolysis mixture in the process plus the amount of the partly hydrolyzed stream in the process may be less than a ratio selected from the group consisting of 2:1, 1:1, 0.9:1, 0.8:1, 0.7:1, 0.6:1, 0.5:1, 0.4:1 and 0.3:1, 0.2:1, and 0.1:1.

It is further disclosed that the pre-treated ligno-cellulosic biomass may be introduced non-continuously into the first vessel.

It is also disclosed that the first hydrolysis mixture may be removed non-continuously from the first vessel.

It is further disclosed that the ratio of the first product stream monomeric sugars concentration to the partly hydrolyzed stream monomeric sugars concentration may be greater than 1.0.

It is also disclosed that the first hydrolysis mixture catalyst to monomeric sugars ratio may be greater than the first product stream catalyst to monomeric sugars ratio.

It is further disclosed that the first product stream catalyst to monomeric sugars ratio divided by the first hydrolysis mixture catalyst to monomeric sugars ratio may be less than a number selected from the group consisting of 1.0, 0.9, 0.8, 0.7, 0.5, 0.4, 0.3, 0.2, and 0.1.

It is also disclosed that the ratio of the amount of enzyme expressed in milligram to the total amount of the beta 1,4 glucans expressed in gram may be in a range selected from the group of ranges consisting of 0.5 to 25, 0.5 to 20, 0.5 to 15, 0.5 to 10, 0.5 to 9, 0.5 to 8, 0.5 to 7.5, 0.5 to 7, 0.5 to 6.5, 0.5 to 6, 0.5 to 5.5, 0.5 to 5, 1 to 5, 1.5 to 5, 2 to 5, 2.5 to 5, 3 to 5, 3.5 to 5, 4 to 5, 4.5 to 5.

DESCRIPTION

Figure 1:
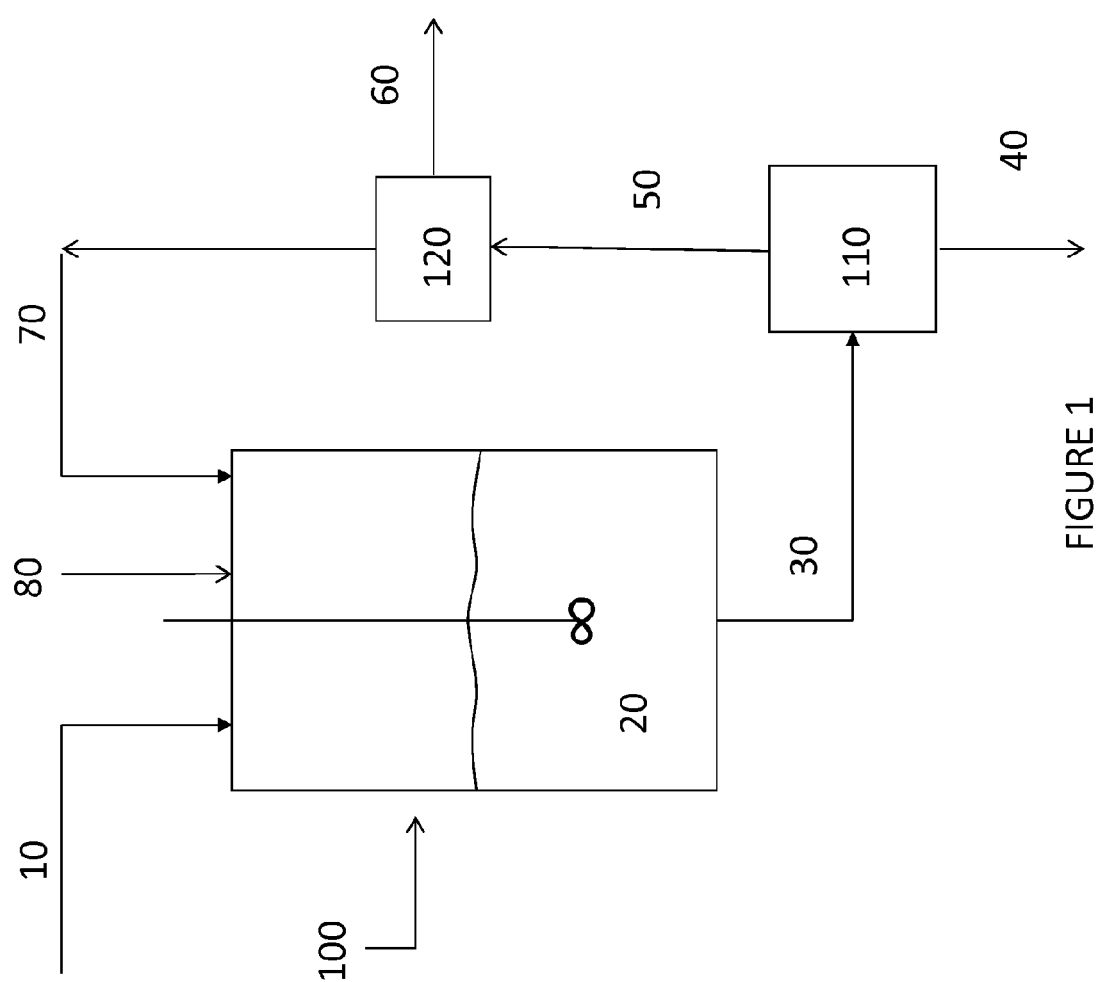
FIG. 1 is an embodiment of the process.

This invention is to an improved process for the production of monomeric sugars streams from the hydrolysis of ligno-cellulosic biomass which relies upon the discovery that removing the monomeric sugars during hydrolysis enhances the production of monomeric sugars. This process will have utility in the second generation biomass hydrolysis processes by increasing the yield of monomeric sugars, in particular during the enzymatic hydrolysis process.

Glucose and xylose are the exemplary monomeric sugars considered in the present disclosure, as they are the main monomeric sugars which are obtained from the hydrolysis of a lignocellulosic biomass. Other monomeric sugars, such as for instance arabinose, may be considered within the scope of the present disclosure.

At a high level, the process can be described as an improved process for the hydrolysis of a pretreated ligno-cellulosic biomass. The pre-treated ligno-cellulosic biomass comprises a solid stream and a liquid stream of the pre-treated ligno-cellulosic biomass.

The solid stream comprises glucans, xylans, which are water insoluble polymeric sugars, and other compounds which are not glucans or xylans. These compounds may comprise other water insoluble polymeric sugars, lignin, proteins, fats, salts and other compounds which are not relevant for the scope of the present invention. Water soluble oligomeric and monomeric sugars, such as for instance glucooligomers, xylooligomers, glucose and xylose, may also be present in the solid stream, preferably in a lower amount with respect to glucans and xylans.

The liquid stream comprises water soluble xylooligomers, water and compounds which are not xylooligomers. These compounds may comprise water soluble oligomeric and monomeric sugars, such as for instance glucooligomers, glucose and xylose; water insoluble polymeric sugars, such as for instance glucans and xylans; lignin, fats, proteins, salts. Each compound which is not xylooligomers, is preferably present in the liquid stream in an amount which is lower than the amount of the xylooligomers on a dry basis. Preferably, the dry matter content of the liquid stream is less than 10%, more preferably less than 5%, even more preferably less than 4%, being less than 3% the most preferred value. Xylooligomers are removed or produced from the xylans of the ligno-cellulosic biomass during the pre-treatment of the ligno-cellulosic biomass.

In the prior art, the hydrolysis of a pre-treated ligno-cellulosic biomass comprising a solid stream and a liquid stream is often conducted on the two streams separately. This configuration has the disadvantage of increasing the equipment needed, and increasing the total cost of the hydrolysis process.

According to other processes disclosed in the prior art, the two streams are hydrolyzed in the same vessel, by mixing the solid stream and all the liquid stream, thereby subjecting the two streams to simultaneously hydrolysis for the same hydrolysis time. This way to conduct the hydrolysis occurs also in the case that the pre-treatment produces a unique stream of pretreated ligno-cellulosic biomass.

It is known in the art that hydrolysis products inhibit, i.e. oligomeric and monomeric sugars, the hydrolysis of the not yet hydrolyzed polymeric sugars, thereby reducing the hydrolysis yield or increasing the time needed to reach a certain yield. For avoiding or limiting the product inhibition effects, different strategies based on the removal of hydrolysis product have been proposed. The removed hydrolysis products, which are in liquid form, are usually replaced by adding water, thereby reducing the sugar concentration of the hydrolyzed streams.

Inventors have found that the hydrolysis of a pre-treated ligno-cellulosic biomass, comprising a solid stream, comprising glucans and xylans, and a liquid stream, comprising xylooligomers, is improved with respect to the methods disclosed in the prior art in the case that the xylooligomers of the liquid stream are hydrolyzed for a hydrolysis time which is shorter that the hydrolysis time of the glucans in the solid stream. It is known in the art that the time needed to hydrolyze xylans and xylooligomers to xylose is shorter than the time needed for hydrolyzing glucans and glucooligomers to glucose.

In the disclosed process, the solid stream produced from the pre-treatment of a ligno-cellulosic biomass and a first portion, but not all, of the liquid stream produced in the pretreatment of the same ligno-cellulosic biomass are hydrolyzed in a first hydrolysis step to create a first hydrolysis mixture. The hydrolysis will occur with the assistance of a hydrolysis catalyst, which could be an acid, a base, at least one enzyme capable of converting glucans to glucose, or mixtures therefore. Then the phrase hydrolysis catalyst is used or catalyst, it is meant the total amount of the catalysts present which convert glucans to glucose. For example, the hydrolysis catalyst often comprises an enzyme, because the catalyst is a mixture of enzymes, known as the enzymatic cocktail. The first hydrolysis mixture comprises monomeric sugars, such as glucose and xylose, and may also comprise water soluble oligomeric sugars, such as glucooligomers and xylooligomers. The monomeric sugars are produced mainly from the hydrolysis of glucans and xylans of the solid stream and xylooligomers of the first portion of the liquid stream; a small fraction of glucose and xylose may be present in the solid stream and or/the liquid stream before the hydrolysis. The first hydrolysis mixture comprises also other compounds which were present in the liquid stream and in the solid stream, such as lignin and a fraction of glucans and xylans, or which may be formed during the hydrolysis. A portion of the monomeric sugars is then removed from the first hydrolysis mixture while the hydrolysis of the glucans of the solid stream is still occurring, thereby producing a first product stream and a partly hydrolyzed stream. Preferably, the removal of the monomeric sugars from the first hydrolysis mixture occurs when the hydrolysis rate of the xylooligomers of the liquid stream has been reduced to less than 50% of the maximum hydrolysis rate, more preferably to less than 40% of the maximum hydrolysis rate, even more preferably to less than 30% of the maximum hydrolysis rate, yet even more preferably to less than 20% of the maximum hydrolysis rate, and most preferably to less than 10% of the maximum hydrolysis rate. Hydrolysis rate is the slope of the curve of xylose concentration in the first hydrolysis mixture versus time while hydrolysis is occurring. Maximum hydrolysis rate usually occurs in the early stage of hydrolysis.

The first product stream comprises monomeric sugars having a first product stream monomeric sugar concentration; it may also comprise a fraction of the hydrolysis catalyst, which is desirable to be as small as possible, thereby the first product stream is characterized also by the first product stream catalyst concentration, which could be 0. The first product stream may be characterized also by the first product stream catalyst to monomeric sugars ratio which is the ratio of first product stream catalyst concentration to the first product stream monomeric sugars concentration.

Monomeric sugars are removed from the first hydrolysis mixture more selectively than hydrolysis catalyst. Stated in other words, the first hydrolysis mixture catalyst to monomeric sugars ratio is greater than or equal to the first product stream catalyst to monomeric sugars ratio.

The partly hydrolyzed stream is the first hydrolysis mixture which has had at least a portion of the monomeric sugar removed. While removing the majority of monomeric sugars from the first hydrolysis mixture is desirable, a certain fraction of monomeric sugars may still be present in the partly hydrolyzed stream. The partly hydrolyzed stream further comprises a fraction of glucans and xylans of the solid stream which have not been hydrolyzed.

In a preferred embodiment, the partly hydrolyzed stream and a second portion of the liquid stream produced in the pre-treatment of the same ligno-cellulosic biomass are hydrolyzed in a second hydrolysis step to create a second hydrolysis mixture. The hydrolysis will occur with the assistance of at least a portion of the hydrolysis catalyst of the first hydrolysis step. Optionally, a fresh hydrolysis catalyst may be added to the second hydrolysis step. If a fresh hydrolysis catalyst is added, preferably it is in an amount which is less than 50%, more preferably less than 40%, even more preferably less than 30%, yet even more preferably less than 20%, and most preferably less than 10% of the amount of the hydrolysis catalyst used in the first hydrolysis step. The second hydrolysis mixture comprises monomeric sugars, such as glucose and xylose, and may also comprise water soluble sugars, such as glucooligomers and xylooligomers. The monomeric sugars are produced mainly from the hydrolysis of glucans and xylans of the partly hydrolyzed stream and xylooligomers of the second portion of the liquid stream; a small fraction of glucose and xylose may be present in the partly hydrolyzed stream and or/the liquid stream before the hydrolysis. The second hydrolysis mixture comprises also other compounds which were present in the liquid stream and in the partly hydrolyzed stream, such as lignin and a fraction of glucans and xylans, or which may be formed during the hydrolysis. A portion of the monomeric sugars is then removed from the second hydrolysis mixture, thereby producing a second product stream comprising monomeric sugars.

A residual stream is created in the removal of the second product stream from the second hydrolysis mixture. The residual stream may comprise not hydrolyzed glucans and xylans, and may be further subjected to subsequent hydrolysis steps.

The disclosed process has the advantage to reduce the concentration of xylose in each hydrolysis step, thereby reducing the product inhibition effects and increasing the hydrolysis yield of the whole process. Moreover, being the liquid fraction added also in the second hydrolysis step, it is reduced the amount of water that has to be added to reach a desired dry matter in the hydrolysis mixtures. As a consequence, the product streams obtained may be more concentrated than in the processes disclosed in the prior art, and less water has to be treated in the downstream processes. Usually, water in excess is removed by thermal processes, or it is treated in a wastewater facility. Both the solutions increase the costs of the end-products.

The first hydrolysis step and the second hydrolysis step may be conducted in a unique vessel, or in two separated vessel. In both cases, the removal of the monomeric sugars from the first hydrolysis mixture may occur outside the first vessel. The removal of the monomeric sugars from the second hydrolysis mixture may occur outside the second vessel.

One embodiment of this process is depicted in FIG. 1, wherein the hydrolysis of at least a portion of the glucans to glucose and at least a portion of the xylooligomers to xylose occurs in a vessel (100), and the removal of the monomeric sugars from the first hydrolysis mixture occurs outside the vessel (110) creating a first product stream (40), with the removal of the monomeric sugars from the hydrolysis mixture creating a partly hydrolyzed stream (50) having a partly hydrolyzed stream monomeric sugars concentration, wherein the partly hydrolyzed stream is the first hydrolysis mixture which has had at least a portion of the monomeric sugars removed, and at least a portion of the partly hydrolyzed stream (50 to 70) is introduced into the vessel. A second portion of the liquid stream (80) is introduced into the vessel (100). In FIG. 1, a portion of the partly hydrolyzed stream is purged from the process at 120 into stream 60. Thus, stream 70 is indeed a portion of the partly hydrolyzed stream 50.

While the reintroduction of the partly hydrolyzed stream is preferred it is not essential. For instance, one embodiment could be that vessel 100 had a membrane splitting creating two or more chambers and the one chamber contained the first hydrolysed mixture 20 and the membrane allowed the monomeric sugars to move into at least one of the other chambers of the while keeping the other glucans in the first hydrolysis mixture to continue being hydrolyzed. In this instance, the monomeric sugars separation is not done outside the vessel.

In the embodiment of FIG. 1, the removal of the monomeric sugars from the first hydrolysis mixture is outside the vessel, also known as the hydrolysis vessel.

The introduction of the feed streams to the vessel can be done on a continuous or non-continuous basis into the vessel (100) and still be a continuous process. What defines the continuous process is that the vessel is not emptied, that is, not all of the first hydrolysis mixture is removed from the vessel and piping of the process including the piping associated with process streams comprising the first hydrolysis mixture (20/30), partly hydrolyzed stream (50/70), but not first product stream (40).

Ligno-cellulosic biomass useful for the invention can be described as follows:

Apart from starch, the three major constituents in plant biomass are cellulose, hemicellulose and lignin, which are commonly referred to by the generic term lignocellulose. Polysaccharide-containing biomasses as a generic term include both starch and lignocellulosic biomasses. Therefore, some types of feedstocks can be plant biomass, polysaccharide containing biomass, and lignocellulosic biomass.

Polysaccharide-containing biomasses according to the present invention include any material containing polymeric sugars e.g. in the form of starch as well as refined starch, cellulose and hemicellulose.

Relevant types of biomasses for deriving the claimed invention may include biomasses derived from agricultural crops selected from the group consisting of starch containing grains, refined starch; corn stover, bagasse, straw e.g. from rice, wheat, rye, oat, barley, rape, sorghum; softwood e.g. *Pinus sylvestris, Pinus radiate*; hardwood e.g. *Salix* spp. *Eucalyptus* spp.; tubers e.g. beet, potato; cereals from e.g. rice, wheat, rye, oat, barley, rape, sorghum and corn; waste paper, fiber fractions from biogas processing, manure, residues from oil palm processing, municipal solid waste or the like. Although the experiments are limited to a few examples of the enumerated list above, the invention is believed applicable to all because the characterization is primarily to the unique characteristics of the lignin and surface area.

The ligno-cellulosic biomass feedstock used in the process is preferably from the family usually called grasses. The proper name is the family known as Poaceae or Gramineae in the Class Liliopsida (the monocots) of the flowering plants. Plants of this family are usually called grasses, or, to distinguish them from other graminoids, true grasses. Bamboo is also included. There are about 600 genera and some 9,000-10,000 or more species of grasses (Kew Index of World Grass Species).

Poaceae includes the staple food grains and cereal crops grown around the world, lawn and forage grasses, and bamboo. Poaceae generally have hollow stems called culms, which are plugged (solid) at intervals called nodes, the points along the culm at which leaves arise. Grass leaves are usually alternate, distichous (in one plane) or rarely spiral, and parallel-veined. Each leaf is differentiated into a lower sheath which hugs the stem for a distance and a blade with margins usually entire. The leaf blades of many grasses are hardened with silica phytoliths, which helps discourage grazing animals. In some grasses (such as sword grass) this makes the edges of the grass blades sharp enough to cut human skin. A membranous appendage or fringe of hairs, called the ligule, lies at the junction between sheath and blade, preventing water or insects from penetrating into the sheath.

Grass blades grow at the base of the blade and not from elongated stem tips. This low growth point evolved in response to grazing animals and allows grasses to be grazed or mown regularly without severe damage to the plant.

Flowers of Poaceae are characteristically arranged in spikelets, each spikelet having one or more florets (the spikelets are further grouped into panicles or spikes). A spikelet consists of two (or sometimes fewer) bracts at the base, called glumes, followed by one or more florets. A floret consists of the flower surrounded by two bracts called the lemma (the external one) and the palea (the internal). The flowers are usually hermaphroditic (maize, monoecious, is an exception) and pollination is almost always anemophilous. The perianth is reduced to two scales, called lodicules, that expand and contract to spread the lemma and palea; these are generally interpreted to be modified sepals.

The fruit of Poaceae is a caryopsis in which the seed coat is fused to the fruit wall and thus, not separable from it (as in a maize kernel).

There are three general classifications of growth habit present in grasses; bunch-type (also called caespitose), stoloniferous and rhizomatous.

The success of the grasses lies in part in their morphology and growth processes, and in part in their physiological diversity. Most of the grasses divide into two physiological groups, using the C3 and C4 photosynthetic pathways for carbon fixation. The C4 grasses have a photosynthetic pathway linked to specialized Kranz leaf anatomy that particularly adapts them to hot climates and an atmosphere low in carbon dioxide.

C3 grasses are referred to as "cool season grasses" while C4 plants are considered "warm season grasses". Grasses may be either annual or perennial. Examples of annual cool season are wheat, rye, annual bluegrass (annual meadowgrass, *Poa annua* and oat). Examples of perennial cool season are orchard grass (cocksfoot, *Dactylis glomerata*), fescue (*Festuca* spp), Kentucky Bluegrass and perennial ryegrass (*Lolium perenne*). Examples of annual warm season are corn, sudangrass and pearl millet. Examples of Perennial Warm Season are big bluestem, indiangrass, bermuda grass and switch grass.

One classification of the grass family recognizes twelve subfamilies: These are 1) anomochlooideae, a small lineage of broad-leaved grasses that includes two genera (*Anomochloa, Streptochaeta*); 2) Pharoideae, a small lineage of grasses that includes three genera, including *Pharus* and *Leptaspis;* 3) Puelioideae a small lineage that includes the African genus *Puelia;* 4) Pooideae which includes wheat, barley, oats, brome-grass (Bronnus) and reed-grasses (*Calamagrostis*); 5) Bambusoideae which includes bamboo; 6) Ehrhartoideae, which includes rice, and wild rice; 7) Arundinoideae, which includes the giant reed and common reed 8) Centothecoideae, a small subfamily of 11 genera that is sometimes included in Panicoideae; 9) Chloridoideae including the lovegrasses (*Eragrostis*, ca. 350 species, including teff), dropseeds (*Sporobolus*, some 160 species), finger millet (*Eleusine coracana* (L.) *Gaertn.*), and the muhly grasses (*Muhlenbergia*, ca. 175 species); 10) Panicoideae including panic grass, maize, sorghum, sugar cane, most millets, fonio and bluestem grasses. 11) Micrairoideae; 12) Danthoniodieae including pampas grass; with *Poa* which is a genus of about 500 species of grasses, native to the temperate regions of both hemispheres.

Agricultural grasses grown for their edible seeds are called cereals. Three common cereals are rice, wheat and maize (corn). Of all crops, 70% are grasses.

Sugarcane is the major source of sugar production. Grasses are used for construction. Scaffolding made from bamboo is able to withstand typhoon force winds that would break steel scaffolding. Larger bamboos and *Arundo donax* have stout culms that can be used in a manner similar to timber, and grass roots stabilize the sod of sod houses. *Arundo* is used to make reeds for woodwind instruments, and bamboo is used for innumerable implements.

The ligno-cellulosic biomass feedstock may also be from woody plants or woods. A woody plant is a plant that uses wood as its structural tissue. These are typically perennial plants whose stems and larger roots are reinforced with wood produced adjacent to the vascular tissues. The main stem, larger branches, and roots of these plants are usually covered by a layer of thickened bark. Woody plants are usually either trees, shrubs, or lianas. Wood is a structural cellular adaptation that allows woody plants to grow from above ground stems year after year, thus making some woody plants the largest and tallest plants.

These plants need a vascular system to move water and nutrients from the roots to the leaves (xylem) and to move sugars from the leaves to the rest of the plant (phloem). There are two kinds of xylem: primary that is formed during primary growth from procambium and secondary xylem that is formed during secondary growth from vascular cambium.

What is usually called "wood" is the secondary xylem of such plants.

The two main groups in which secondary xylem can be found are:
1) conifers (Coniferae): there are some six hundred species of conifers. All species have secondary xylem, which is relatively uniform in structure throughout this group. Many conifers become tall trees: the secondary xylem of such trees is marketed as softwood.
2. angiosperms (Angiospermae): there are some quarter of a million to four hundred thousand species of angiosperms. Within this group secondary xylem has not been found in the monocots (e.g Poaceae). Many non-monocot angiosperms become trees, and the secondary xylem of these is marketed as hardwood.

The term softwood is used to describe wood from trees that belong to gymnosperms. The gymnosperms are plants with naked seeds not enclosed in an ovary. These seed "fruits" are considered more primitive than hardwoods. Softwood trees are usually evergreen, bear cones, and have needles or scalelike leaves. They include conifer species e.g. pine, spruces, firs, and cedars. Wood hardness varies among the conifer species.

The term hardwood is used to describe wood from trees that belong to angiosperm family. Angiosperms are plants with ovules enclosed for protection in an ovary. When fertilized, these ovules develop into seeds. The hardwood trees are usually broad-leaved; in temperate and boreal latitudes they are mostly deciduous, but in tropics and subtropics mostly evergreen. These leaves can be either simple (single blades) or they can be compound with leaflets attached to a leaf stem. Although variable in shape all hardwood leaves have a distinct network of fine veins. The hardwood plants include e.g. Aspen, Birch, Cherry, Maple, Oak and Teak.

Therefore a preferred ligno-cellulosic biomass may be selected from the group consisting of the grasses and woods. A preferred ligno-cellulosic biomass may be selected from the group consisting of the plants belonging to the conifers, angiosperms, Poaceae and/or Gramineae families. Another preferred lignocellulosic biomass may also be that biomass having at least 10% by weight of it dry matter as cellulose, or more preferably at least 5% by weight of its dry matter as cellulose.

The ligno-cellulosic biomass will also comprise carbohydrate(s) selected from the group of carbohydrates based upon the glucose, xylose, and mannose monomers. Being derived from ligno-cellulosic biomass, means that the ligno-cellulosic biomass of the feed stream will comprise glucans and xylans and lignin.

Glucans include the water insoluble polymers of glucose in the ligno-cellulosic biomass. Of particular interest is 1,4 beta glucan which is particular to cellulose, as opposed to 1,4 alpha glucan. The amount of 1,4 beta glucan(s) present in the pre-treated ligno-cellulosic biomass should be at least 5% by weight of the pre-treated ligno-cellulosic biomass on a dry basis, more preferably at least 10% by weight of the pre-treated ligno-cellulosic biomass on a dry basis, and most preferably at least 15% by weight of the pre-treated ligno-cellulosic biomass on a dry basis.

Xylans include the water insoluble polymers of xylan in the pre-treated ligno-cellulosic biomass composition.

The pre-treated ligno-cellulosic biomass can be free of starch, substantially free of starch, or have a starch content of 0. Starch, if present, can be less than 75% by weight of the dry content. There is no preferred starch range as its presence is not believed to affect the hydrolysis to glucose. Ranges for the amount of starch, if present, are between 0 and 75% by weight of the dry content, 0 to 50% by weight of the dry content, 0 to 30% by weight of the dry content and 0 to 25% by weight of the dry content.

The pre-treatment used to pre-treat the pre-treated ligno-ceullosic biomass is used to ensure that the structure of the lignocellulosic content is rendered more accessible to the catalysts, such as enzymes, and at the same time the concentrations of harmful inhibitory by-products such as acetic acid, furfural and hydroxymethyl furfural remain substantially low.

There are several strategies to pre-treat the biomass, many of which may yet be invented. In any event, to be pre-treated, the ligno-cellulosic biomass have its ligno-cellulosic content more accessible than the ligno-cellulosic content prior to pretreatment.

The current strategies of pre-treatment are subjecting the lignocellulosic material to temperatures between 110-250° C. for 1-60 min e.g.:
  Hot water extraction
  Multistage dilute acid hydrolysis, which removes dissolved material before inhibitory substances are formed
  Dilute acid hydrolysis at relatively low severity conditions
  Alkaline wet oxidation
  Steam explosion
  Almost any pre-treatment with subsequent detoxification If a hydrothermal pre-treatment is chosen, the following conditions are preferred:
  Pre-treatment temperature: 110-250° C., preferably 120-240° C., more preferably 130-230° C., more preferably 140-220° C., more preferably 150-210° C., more preferably 160-200° C., even more preferably 170-200° C. or most preferably 180-200° C.
  Pre-treatment time: 1-60 min, preferably 2-55 min, more preferably 3-50 min, more preferably 4-45 min, more preferably 5-40 min, more preferably 5-35 min, more preferably 5-30 min, more preferably 5-25 min, more preferably 5-20 min and most preferably 5-15 min.
  Dry matter content after pre-treatment is preferably at least 20% (w/w). Other preferable higher limits are contemplated as the amount of biomass to water in the pre-treated ligno-cellulosic feedstock be in the ratio ranges of 1:4 to 9:1;

1.3.9 to 9:1, 1:3.5 to 9:1, 1:3.25 to 9:1, 1:3 to 9:1, 1:2.9 to 9:1, 1:2 to 9:1, 1.15 to 9:1, 1:1 to 9:1, and 1:0.9 to 9:1.

Polysaccharide-containing biomasses according to the present invention include any material containing polymeric sugars e.g. in the form of starch as well as refined starch, cellulose and hemicellulose. However, as discussed earlier, the starch is not a primary component.

A preferred pre-treatment process is the two step soak/extract followed by steam explosion as describe below.

A preferred pretreatment of a ligno-cellulosic biomass include a soaking of the ligno-cellulosic biomass feedstock and a steam explosion of at least a part of the soaked ligno-cellulosic biomass feedstock.

The soaking occurs in a substance such as water in either vapor form, steam, or liquid form or liquid and steam together, to produce a product. The product is a soaked biomass containing a first liquid, with the first liquid usually being water in its liquid or vapor form or some mixture.

This soaking can be done by any number of techniques that expose a substance to water, which could be steam or liquid or mixture of steam and water, or, more in general, to water at high temperature and high pressure. The temperature should be in one of the following ranges: 145 to 165° C., 120 to 210° C., 140 to 210° C., 150 to 200° C., 155 to 185° C., 160 to 180° C. Although the time could be lengthy, such as up to but less than 24 hours, or less than 16 hours, or less than 12 hours, or less than 9 hours or less than 6 hours; the time of exposure is preferably quite short, ranging from 1 minute to 6 hours, from 1 minute to 4 hours, from 1 minute to 3 hours, from 1 minute to 2.5 hours, more preferably 5 minutes to 1.5 hours, 5 minutes to 1 hour, 15 minutes to 1 hour.

If steam is used, it is preferably saturated, but could be superheated. The soaking step can be batch or continuous, with or without stirring. A low temperature soak prior to the high temperature soak can be used. The temperature of the low temperature soak is in the range of 25 to 90° C. Although the time could be lengthy, such as up to but less than 24 hours, or less than 16 hours, or less than 12 hours, or less than 9 hours or less than 6 hours; the time of exposure is preferably quite short, ranging from 1 minute to 6 hours, from 1 minute to 4 hours, from 1 minute to 3 hours, from 1 minute to 2.5 hours, more preferably 5 minutes to 1.5 hours, 5 minutes to 1 hour, 15 minutes to 1 hour.

Either soaking step could also include the addition of other compounds, e.g. $H_2SO_4$, $NH_3$, in order to achieve higher performance later on in the process.

The product comprising the first liquid is then passed to a separation step where the first liquid is separated from the soaked biomass. The liquid will not completely separate so that at least a portion of the liquid is separated, with preferably as much liquid as possible in an economic time frame. The liquid from this separation step is known as the first liquid stream comprising the first liquid. The first liquid will be the liquid used in the soaking, generally water and the soluble species of the feedstock. These water soluble species are glucan, xylan, galactan, arabinan, glucolygomers, xylooligomers, galactolygomers and arabinolygomers. The solid biomass is called the first solid stream as it contains most, if not all, of the solids.

The separation of the liquid can again be done by known techniques and likely some which have yet been invented. A preferred piece of equipment is a press, as a press will generate a liquid under high pressure.

The first solid stream is then steam exploded to create a steam exploded stream, comprising solids and a second liquid. Steam explosion is a well known technique in the biomass field and any of the systems available today and in the future are believed suitable for this step. The severity of the steam explosion is known in the literature as Ro, and is a function of time and temperature and is expressed as $$Ro = t\exp[(T-100)/14.75]$$

with temperature, T expressed in Celsius and time, t, expressed in common units, e.g. minutes.

The formula is also expressed as Log(Ro), namely $$\text{Log}(Ro) = \text{Ln}(t) + [(T-100)/14.75].$$

Log(Ro) is preferably in the ranges of 2.8 to 5.3, 3 to 5.3, 3 to 5.0 and 3 to 4.3.

The steam exploded stream may be optionally washed at least with water and there may be other additives used as well. It is conceivable that another liquid may be used in the future, so water is not believed to be absolutely essential. At this point, water is the preferred liquid and if water is used, it is considered the third liquid. The liquid effluent from the optional wash is the third liquid stream. This wash step is not considered essential and is optional.

The washed exploded stream is then processed to remove at least a portion of the liquid in the washed exploded material. This separation step is also optional. The term at least a portion is removed, is to remind one that while removal of as much liquid as possible is desirable (pressing), it is unlikely that 100% removal is possible. In any event, 100% removal of the water is not desirable since water is needed for the subsequent hydrolysis reaction. The preferred process for this step is again a press, but other known techniques and those not invented yet are believed to be suitable. The products separated from this process are solids in the second solid stream and liquids in the second liquid stream.

The solid stream of the disclosed process comprises the steam exploded stream and/or at least a portion of the washed steam exploded stream. The liquid stream comprises the first liquid stream, and/or the second liquid stream, and/or the third liquid stream.

The solid stream and a first portion of the liquid stream are introduced into vessel (100). The solid stream and the first portion of the liquid stream may be mixed together to form a unique stream (100) which is introduced into the vessel. Other components, needed to reach the desired hydrolysis conditions, such as water to reach a desired dry matter content, may be added prior to, during and/or after the mixing. The solid stream and a first portion of the liquid stream may be introduced into vessel (100) as two separated stream, and other components may be introduced to one or both the streams separately or to the vessel. After the solid stream and the first portion of the liquid stream of the pre-treated ligno-cellulosic feedstock are introduced into vessel (100), they undergo hydrolysis of at least a portion of the glucans in the solid stream to glucose at least a portion of the xylooligomers in the first portion of the liquid stream to xylose to create a first hydrolysis mixture (20) inside the vessel (100). This first hydrolysis mixture (20) will have a monomeric sugars concentration called the first hydrolysis mixture monomeric sugars concentration. In a batch process the first hydrolysis mixture monomeric sugars concentration will vary with time. In a true continuous process, the first hydrolysis mixture monomeric sugars concentration will not vary substantially with time. In any event, when the specification calls for a ratio of two concentrations or amounts, it is taken that the samples are taken at the same time or over the same time interval.

The hydrolysis of the glucans to glucose and the xylooligomers to xylose can be done by any of the known process, and those yet to be invented, and includes but is not limited to enzymatic hydrolysis, acid hydrolysis, and base hydrolysis. Enzymatic hydrolysis refers the use of at least one enzyme to convert the glucans, in particular the 1,4 beta glucans, to glucose. These enzymes are well known in the art and more are developed and discovered each year.

It is also known from WO 2010/113129, the teachings of which are incorporated by reference in their entirety that it is preferable for the ratio of the amount of the pre-treated ligno-cellulosic biomass in the feedstream on a dry basis added to the vessel 100 to the amount of the amount of first hydrolysis mixture (20) remaining in the vessel plus the amount of the partly hydrolyzed stream (70) added to the vessel be less than a ratio selected from the group consisting of 2:1, 1:1, 0.9:1, 0.8:1, 0.7:1, 0.6:1, 0.5:1, 0.4:1 and 0.3:1, 0.2:1, and 0.1:1.

For instance, if 5 Kg of dry pre-treated ligno-cellulosic biomass is added to vessel (100) in one hour and 4 Kg of the partly hydrolyzed stream (70) is added per hour, then for a ratio of 1:1, there should be 1 Kg of first hydrolysis mixture (20) in the vessel. For a ratio of 0.5 to 1, there should 6 Kg of the hydrolysis mixture in the vessel. This allows for the more rapid hydrolysis of the pre-treated ligno-cellulosic biomass in the vessel (100).

At least a portion of the first hydrolysis mixture (20) is removed from the vessel (100) to create a first hydrolysis mixture stream (30) and optionally leaving an amount of the hydrolysis mixture to remain in the vessel (100). The hydrolysis mixture stream may be removed in a continuous or non-continuous manner.

The next step is to remove (110) at least a portion of the monomeric sugars from the first hydrolysis mixture (20/30). This creates at least a first product stream (40) and a partly hydrolyzed stream (50). The ratio of the first product stream monomeric sugars concentration (40) to partly hydrolyzed stream monomeric sugars concentration should greater than or equal to 1.0.

In the case where the ratio is equal to 1, the removal of monomeric sugars can be done by splitting the first hydrolysis mixture stream obviating the use of a filter or centrifuge. While the ratio can be equal to 1, it is preferred that the ratio be less than 1.0, with less than 0.90 being more preferred with less than 0.80 being even more preferred, with less than 0.60 being an even more preferred amount with less than 0.5 being the most preferred.

The removal of monomeric sugars from a liquid or water based composition (110) is well known in the art and can be done by any technique known, and those to be discovered in the future. At least three ways of separating contemplated by the inventors are centrifugation singly or in combination with a filtration step which can comprise a filtration technique selected from the group consisting of nano-filtration, ultra high filtration, and reverse osmosis.

Another parameter is that the when the monomeric sugars are removed from the first hydrolysis mixture stream, that the majority of the catalysts, in particular the enzymes and to the extent practical, is not comprised in the first product stream, but they remain in the partly recycled stream. Optionally, catalysts may remain in the first hydrolysis mixture. For example, the first hydrolysis mixture will have an amount of hydrolysis catalyst. The amount of hydrolysis catalyst divided by the amount of the first hydrolysis mixture by mass is called the first hydrolysis mixture hydrolysis catalyst concentration. It can also be expressed as grams catalyst per unit volume of mixture as well. When comparisons of concentrations are made, the units are to be consistent, such as is well known in the art.

The first hydrolysis mixture will have first hydrolysis mixture catalyst to monomeric sugars ratio which is the ratio of the amount by weight of the catalyst in first hydrolysis mixture to the amount by weight of monomeric sugars in the first hydrolysis mixture. The first hydrolysis mixture catalyst to monomeric sugars ratio is also the ratio of the first hydrolysis mixture catalyst concentration to the first hydrolysis mixture monomeric sugars concentration.

The first product stream will have a first product stream catalyst concentration. If the amount of catalyst in the first product stream is 0, then first product stream catalyst concentration is 0. 0 is a preferred value for the first product stream catalyst concentration. The first product stream will have a first product stream catalyst to monomeric sugars ratio which is the ratio of the amount by weight of the first product stream hydrolysis catalyst to the amount by weight of the monomeric sugars in the first product stream Like the first hydrolysis mixture catalyst to monomeric sugars ratio, the first product stream catalyst to monomeric sugars ratio is also the ratio of first product stream catalyst concentration to the first product stream monomeric sugars concentration. The values are determined at the same time and immediately prior to the removal of the monomeric sugars and immediately after the removal of the monomeric sugars, respectively.

Since one objective of the monomeric sugars removal is to keep the catalyst for further use, the catalyst should not follow the removed monomeric sugars but stay in the stream to be reintroduced into the vessel. Therefore, it is preferred that the first hydrolysis mixture catalyst to monomeric sugars ratio is greater than or equal to the first product stream catalyst to monomeric sugars ratio. In another embodiment it is even more preferred that the first hydrolysis mixture catalyst to monomeric sugars ratio is greater than the first product stream catalyst to monomeric sugars ratio.

The more monomeric sugars are removed and the catalyst recirculated, it is believed the process will improve. Therefore it is preferable that the first product stream catalyst to monomeric sugars ratio divided by the first hydrolysis mixture catalyst to monomeric sugars ratio is less than a number selected from the group consisting of 1.0, 0.9, 0.8, 0.7, 0.5, 0.4, 0.3, 0.2, and 0.1.

Figure 2:
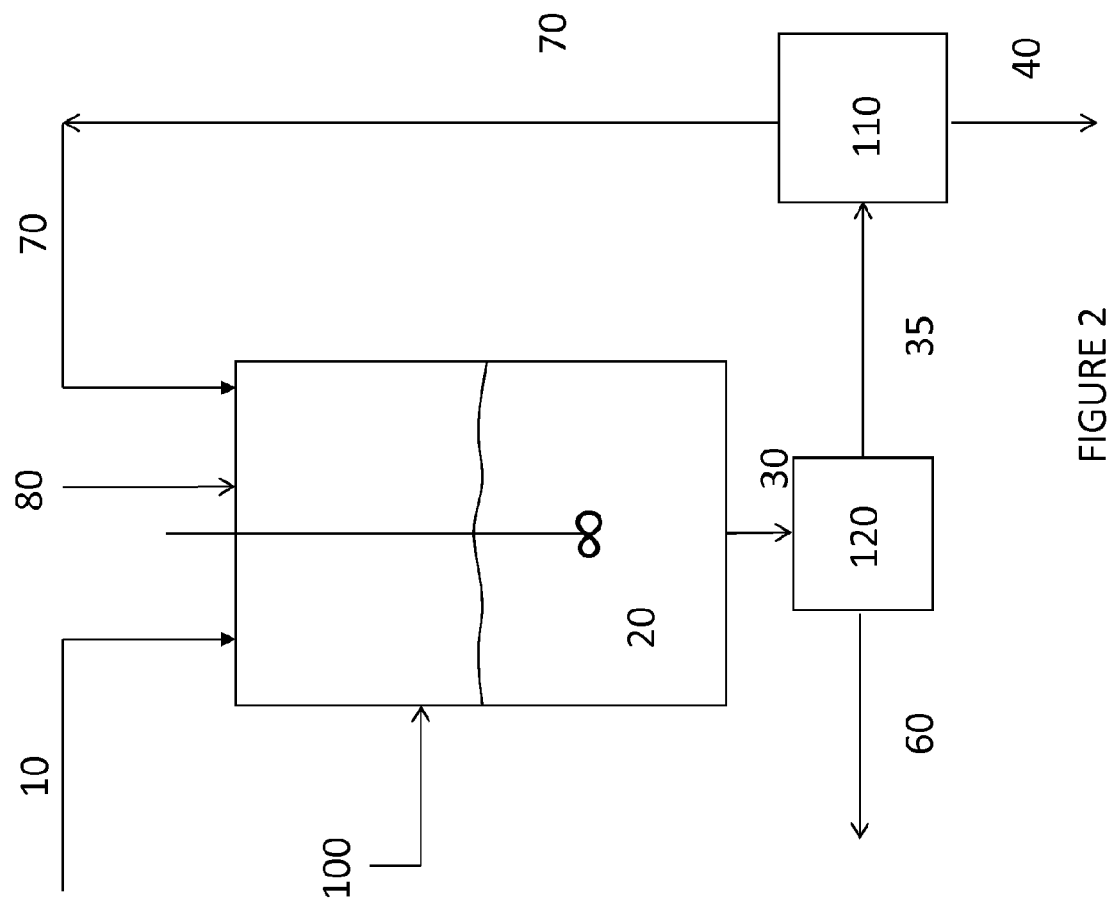
FIG. 2 is another embodiment of the process showing a different point of purging.
Figure 3:
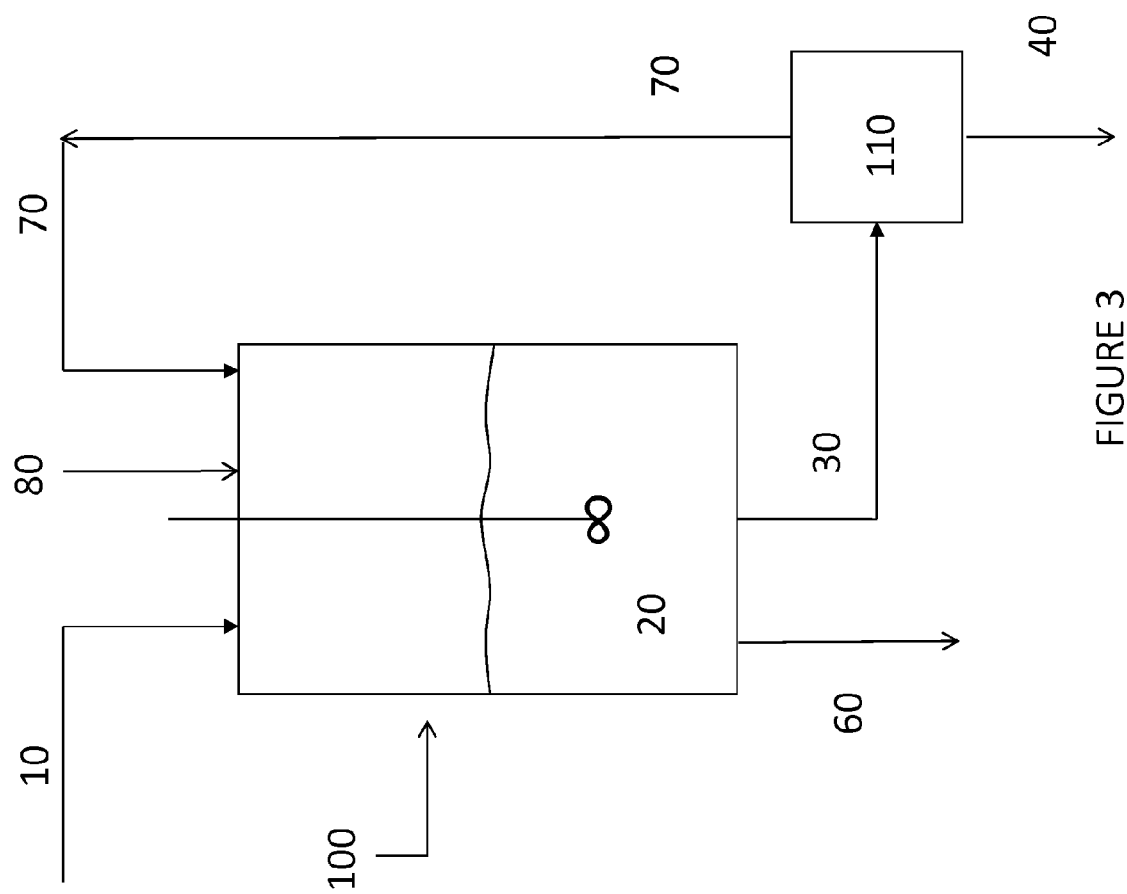
FIG. 3 is another embodiment of the process showing a different point of purging.

The process can be further enhanced as shown in the FIGS. 1-3 by purging or removing at least a portion of the material in the process, wherein the purged material is selected from the group consisting of the first hydrolysis mixture, the first hydrolysis mixture stream and the glucose recycle stream In FIG. 1, a portion of the partly hydrolyzed stream is diverted at 120 into purge stream 60 and with the remainder of the partly hydrolyzed stream (70) introduced into the vessel. Typically the purge is just a splitting of one stream into two streams, with the purge stream being isolated from the process. In FIG. 1, the components of the first hydrolyzed stream (50), is split into the first product stream (60) and the partly hydrolyzed stream (70), so that the concentrations of the components of the two streams are the same.

Thus some material has been purged from the process. Thus by purging or to purge, it is meant to remove the material from the process thus to accommodate both physically and chemically more feedstock. The purging can be done with valves, elbows, tees, or any technique known in the art and yet to be invented.

The differences among FIGS. 1, 2, and 3 is the location of the purge stream. In FIG. 1, the purge is done on the partly hydrolyzed stream. In FIG. 2, the purge is done on the first hydrolysis mixture after it has left the vessel. In FIG. 3, the purge is done by diverting a portion of the first hydrolysis mixture directly from the vessel.

The purge can also be related to the those components which are not glucans or xylans and the purged material can be described as at least a portion of the glucans, xylans, and compounds which are not glucans or xylans are purged or removed from the process.

The ratio of the amount, or mass, of the purged stream to the amount, or mass, of partly hydrolyzed stream is not so critical but should be in a range selected from the group of ranges consisting of 1:99 to 99:1, 5:95 to 50:50, 50:50 to 95:5, 10:90 to 90:10, 20:80 to 80:20, 30:70 to 70:30, and 40:60 to 60:40.

In the embodiments of FIGS. 1 to 3, optionally a second portion of the liquid stream (80) may be added to the vessel (100) and mixed with the partly hydrolyzed stream (70). The partly hydrolyzed stream and the second portion of the liquid stream may be mixed together to form a unique stream which is introduced into the vessel. Other components, needed to reach the desired hydrolysis conditions, such as water to reach a desired dry matter, may be added prior to, during and/or after the mixing. The partly hydrolyzed stream and the second portion of the liquid stream may be introduced into vessel (100) as two separated stream, and other components may be introduced to one or both the streams separately or to the vessel. After that the partly hydrolyzed stream and the second portion of the liquid stream of the pre-treated ligno-cellulosic feedstock are introduced into vessel (100), they undergo hydrolysis of at least a portion of the glucans in the partly hydrolyzed stream to glucose at least a portion of the xylooligomers in the second portion of the liquid stream to xylose to create a second hydrolysis mixture (20) inside the vessel (100). Again, a second monomeric sugars product stream, comprising at least a portion of glucose and xylose of the second hydrolysis mixture, may be created from the second hydrolysis mixture. A second partly hydrolyzed mixture may also be obtained, by means of separation and purging techniques previously described in the present specification. The second partly hydrolyzed mixture may be reused for a further hydrolysis step or removed from the process.

Figure 4:
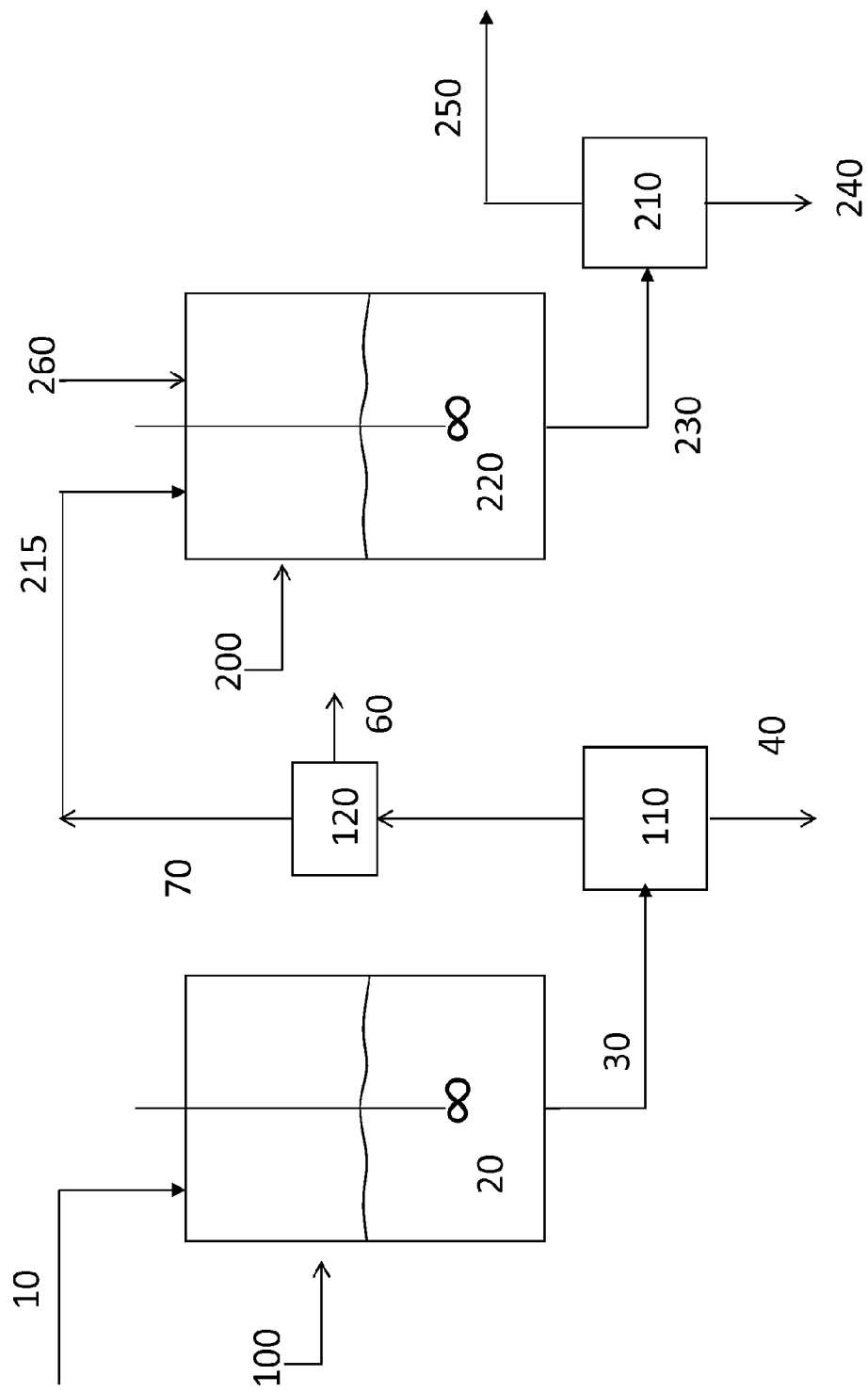
FIG. 4 is another embodiment of the process showing a two vessel configuration.

In the exemplary embodiment of FIG. 4 the two hydrolysis steps are conducted in two separated vessels. At least a portion (215) of partly hydrolyzed stream (70) and a second portion of the liquid stream are introduced into the second vessel (200), where they undergo hydrolysis of at least a portion of the glucans in the partly hydrolyzed stream to glucose at least a portion of the xylooligomers in the second portion of the liquid stream to xylose to create a second hydrolysis mixture (220) inside the vessel (200). Stream 230 is the corollary to stream 30 of the previous process. A second monomeric sugars product stream (240), comprising at least a portion of glucose and xylose of the second hydrolysis mixture, may be created from the second hydrolysis mixture at (210). A second partly hydrolyzed mixture (250) may also be obtained, by means of separation and purging techniques previously described in the present specification. 260 of FIG. 4 is the same stream as stream 80 in FIGS. 1-3.

The concept of this invention is not limited by embodiments described above, but the general principles should be open to modifications and still be considered under the claims of this invention.

EXPERIMENTAL

Analytical Measurements
Analytical measurements were performed according to the following NREL standards
NREL Analytical Method
Determination of Structural Carbohydrates and Lignin in Biomass
   Laboratory Analytical Procedure (LAP) Issue Date: Apr. 25, 2008
   Technical Report NREL/TP-510-42618 Revised April 2008
Determination of Extractives in Biomass
   Laboratory Analytical Procedure (LAP) Issue Date: Jul. 17, 2005
   Technical Report NREL/TP-510-42619 January 2008
Preparation of Samples for Compositional Analysis
   Laboratory Analytical Procedure (LAP) Issue Date: Sep. 28, 2005
   Technical Report NREL/TP-510-42620 January 2008
Determination of Total Solids in Biomass and Total Dissolved Solids in Liquid Process Samples
   Laboratory Analytical Procedure (LAP) Issue Date: Mar. 31, 2008
   Technical Report NREL/TP-510-42621 Revised March 2008
Determination of Ash in Biomass
   Laboratory Analytical Procedure (LAP) Issue Date: Jul. 17, 2005
   Technical Report NREL/TP-510-42622 January 2008
Determination of Sugars, Byproducts, and Degradation Products in Liquid Fraction Process Samples
   Laboratory Analytical Procedure (LAP) Issue Date: Dec. 8, 2006
   Technical Report NREL/TP-510-42623 January 2008
Determination of Insoluble Solids in Pretreated Biomass Material
   Laboratory Analytical Procedure (LAP) Issue Date: Mar. 21, 2008
   NREL/TP-510-42627 March 2008
PRETREATMENT PROCEDURE Wheat straw was introduced into a continuous reactor and subjected to a soaking treatment at a temperature of 155° C. for 65 minutes. The soaked mixture was separated in a soaked liquid and a fraction containing the solid soaked raw material by means of a press. The fraction containing the solid soaked raw material was subjected to steam explosion at a temperature of 190° C. for a time of 4 minutes to produce a solid stream.

The pre-treatment produced a soaked liquid and a solid stream in a ratio liquid stream:solid stream of 2.8:1.

The dry matter of the soaked liquid was 3.9%, and the composition by weight on dry basis of the soaked liquid is reported in Table 1.

TABLE 1

Composition of the soaked liquid produced from the soaking treatment.

| | |
|---|---|
| Glucose | 0.0% |
| Xylose | 1.3% |
| Acetic acid | 5.5% |
| Glucoligomers | 7.5% |
| Xyloligomers | 24.2% |
| Insoluble glucans | 0.0% |
| Insoluble xylans | 0.0% |
| Others | 61.4% |

The dry matter of the solid stream was 55.6%, and the composition by weight on dry basis of the solid stream is reported in Table 2.

TABLE 2

Composition of the solid stream produced from the steam explosion.

| | |
|---|---|
| Glucose | 0.9% |
| Xylose | 0.0% |
| Acetic acid | 0.2% |
| Glucoligomers | 0.4% |
| Xyloligomers | 3.6% |
| Insoluble glucans | 42.9% |
| Insoluble xylans | 9.0% |
| Others | 43.0% |

Soaked liquid was subjected to a membrane filtration step to remove a portion of acetic acid. By membrane nanofiltration, the soaked liquid is also concentrated.

First, soaked liquids were subjected to a preliminary pre-separation step to remove solids, by means of centrifugation and macro filtration (bag filter with filter size of 1 micron). Centrifugation was performed by means of a Alfa Laval CLARA 80 centrifuge at 8000 rpm.

Pre-separated liquids were subjected to nanofiltration by means of a Alfa Laval 2.5" equipment (membrane code NF99 2517/48), according to the following procedure.

Permeate flow stability was checked by means of flushing with de-mineral water, at room temperature (25° C.) and 4 bar. Flow rate of the permeate was measured. An amount of 192 liter of soaked liquid were inserted in the feed tank. Before test, the system was flushed for 5 minutes, without pressure, in order to remove the water.

The system was set at the operating conditions (pressure: 25-30 bar, temperature: 30-35° C.).

Retentate stream was recycled in the feed tank and permeate stream was dumped.

The test was run until the volume of liquid in the feed tank was reduced up to 62.5% of the initial soaked liquid volume, corresponding to 72 liters of permeate and 120 liters of retentate.

Nanofiltered permeate and retentate were collected.

Nanofiltered retentate is the liquid stream used in the following hydrolysis experiments.

The dry matter of the liquid stream was 8.7%, corresponding to a volume ratio of soaked liquid to liquid stream of 2.7, and the composition of the liquid stream on a dry basis is reported in Table 3. The amount of acetic acid in the liquid stream is significantly lower than in the soaked liquid.

TABLE 3

Composition of the liquid stream used in hydrolysis experiments.

| | |
|---|---|
| Glucose | 0.0% |
| Xylose | 1.4% |
| Acetic acid | 3.0% |
| Glucoligomers | 6.4% |
| Xyloligomers | 24.6% |
| Insoluble glucans | 0.0% |
| Insoluble xylans | 0.0% |
| Others | 64.6% |

Control Experiment 1 (CE1)

The solid stream and the liquid stream, in a ratio as produced from the pre-treatment, were subjected to hydrolysis in standard batch configuration.

An amount of 0.202 Kg of solid stream and an amount of 0.202 Kg of liquid stream were mixed in a reactor. An amount of 0. 1.092 kg of water was added in order to reach the dry matter of about 6%. An amount of enzyme solution of 100 mg per gram of glucans in the solid stream was added and pH was set to 5 using a KOH solution (2 M).

Hydrolysis was performed at 50° C. for 48 hours and the composition of the hydrolysis mixture was analyzed at different time during the hydrolysis.

Figure 5:
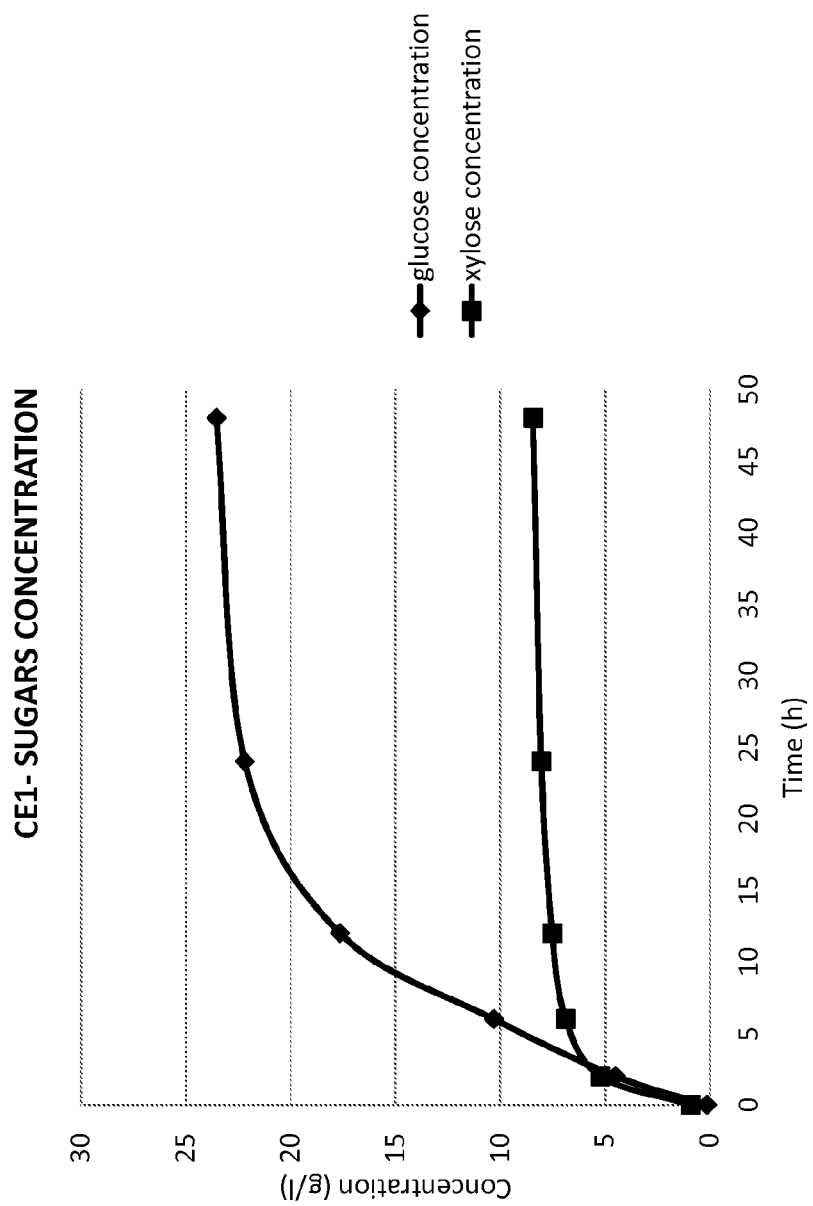
FIG. 5 graphically depicts the glucose and xylose concentration in CE1.

FIG. 5 reports the glucose and xylose concentration during hydrolysis. Glucose concentration and xylose concentration at 24 h were 22 g/l and 8 G/l respectively corresponding to ah hydrolysis yield of 78% and 75% respectively. Final glucose concentration at 48 h was 24 g/l and final xylose concentration was 8 g/l, corresponding to an hydrolysis yield of 81% and 80% respectively.

Hydrolysis yield were calculated with respect to the amount of xylans and glucans in the liquid stream and the solid stream entering enzymatic hydrolysis.

From FIG. 5 it is evident that xylose formation rate is significant faster than glucose formation rate and for this reason the most important factor taken in consideration to evaluate the improvement is the glucose release and the glucose yield.

Control Experiment 2 (CE2)

The solid stream and the liquid stream were subjected to a two-step hydrolysis, recycling the enzymes and the partially hydrolyzed solid stream and separating the hydrolysis products between the two steps. All the liquid stream is introduced in the first hydrolysis step.

An amount of 0.202 Kg of solid stream and an amount of 0.202 Kg of liquid stream were introduced in a reactor, in a ratio as produced from the pre-treatment. An amount of 1.092 Kg of water was added to reach a dry matter of about 6%.

An amount of enzyme solution of 100 mg per gram of glucans in the solid stream was added and pH was set to 5 using a KOH solution (2 M). Hydrolysis was performed at 50° C. for a first hydrolysis time of 24 hours and the composition of the first hydrolysis mixture was analyzed at different time. At the end of the first hydrolysis time, it was obtained a first hydrolysis stream with a glucose concentration of 23 g/l and a xylose concentration of 8 g/l; the hydrolysis yield reached is of 79% for glucans and 78% for xylans. Hydrolysis mixture was removed from the reactor and centrifuged in a Thermoscientific centrifuge at 9500 rpm for 10 minutes and separated in a first liquid hydrolyzed portion, comprising the most part of solubilized sugars, and a first solid portion.

The activities of enzymes and the amount of proteins in the first liquid hydrolyzed portion was analyzed in order to study the amount of active enzymes, which were no more available for the second hydrolysis step. In Table 4 the relative variation of the enzyme activity with respect to the corresponding starting values are reported. The concentration of protein in the liquid fraction at the end of the first hydrolysis step was 13.5% of the starting protein concentration.

TABLE 4

Activity of enzymes in the liquid fraction of the hydrolysis mixture at different time.

| | Time, h | | | | |
|---|---|---|---|---|---|
| | 0 Soluble enzymes, % | 1 | 5 | 24 | 48 |
| Cellulase | 100% | 12% | 7% | 7% | 7% |
| Beta-glucosidase | 100% | 14% | 3% | 1% | 1% |
| Xylanase | 100% | 29% | 16% | 5% | 6% |

The first solid fraction was inserted in the reactor for a second hydrolysis step.

An amount of 0.389 Kg of water was added to the reactor, to reestablishing a dry matter of about 6% and hydrolysis was continued for a second hydrolysis time of 24 hours, at the same conditions of the first hydrolysis step, in the presence of the enzymes recycled in the first solid fraction. No new enzymes were added. At the end of the second hydrolysis time, it was obtained a second hydrolysis stream with a glucose concentration of 1.6 g/l and a xylose concentration of 0.4 g/l.

Figure 6:
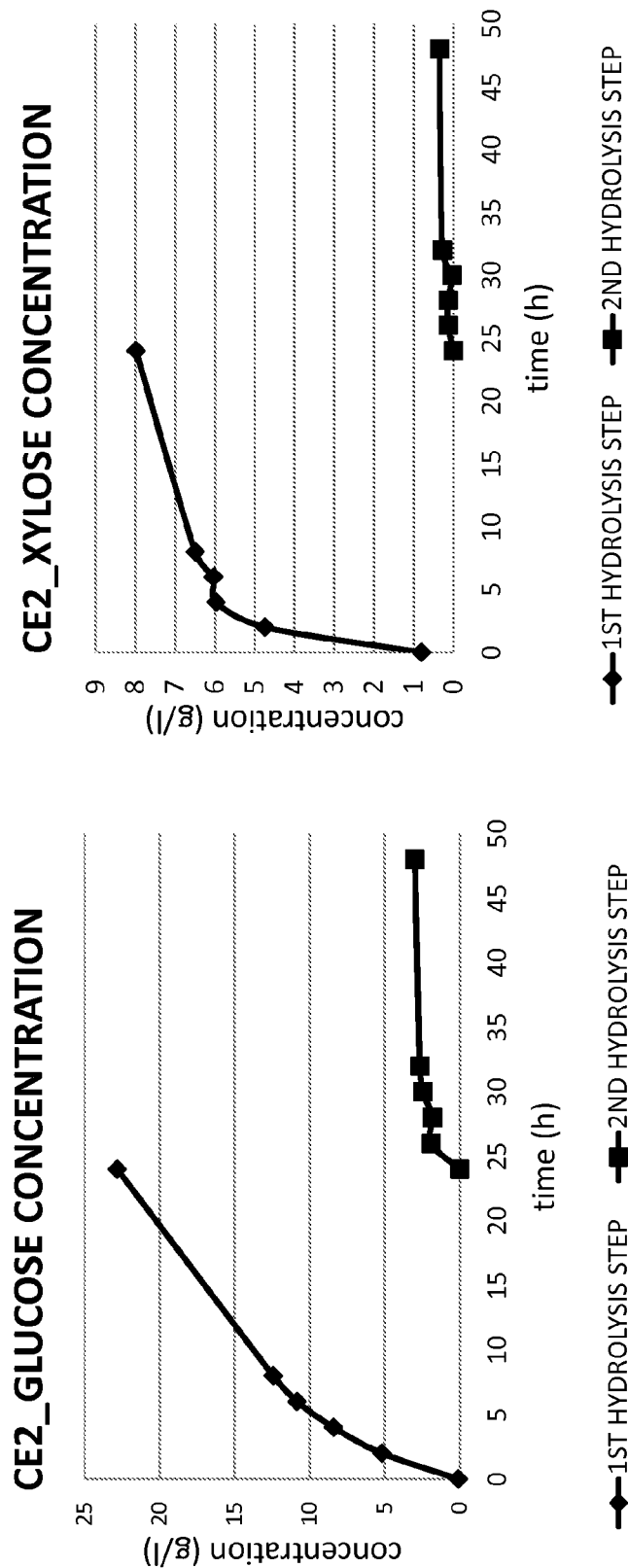
FIG. 6 graphically depicts glucose and xylose concentration in CE2.

FIG. 6 reports the glucose and xylose concentration during the two steps of enzymatic hydrolysis.

The streams from the two hydrolysis steps were mixed for comparison with CE1. Table 5 reports the composition of the total stream on a dry basis. The global dry matter was 4.5%.

TABLE 5

Composition of the total stream of CE2

| | TOTAL COMPOSITION |
|---|---|
| glucose | 37.6% |
| xylose | 11.5% |
| acetic acid | 1.2% |
| glucoligomers | 1.4% |
| xyloligomers | 2.2% |
| acetyls | 0.2% |
| insoluble glucans | 0.2% |
| insoluble xylans | 0.0% |
| other | 45.8% |

The glucose concentration of the total stream was 25 g/l, and the xylose concentration was 9 g/l corresponding to a global hydrolysis yield of 90% and 90% for glucans and xylans respectively.

CE2 demonstrates that removal of product inhibition with enzymes recycle improves the yield of the process with respect to standard batch hydrolysis of CE1. On the other hand, the addition of water in the second hydrolysis step, needed to re-establishing the operating dry matter, produces a global stream less concentrated than in CE1.

Working Experiment 1 (WE1)

The solid stream and the liquid stream were subjected to a two-step hydrolysis with enzymes recycle and products separation as in CE2, with the difference that a first portion of the liquid stream is introduced in the first hydrolysis step and a second portion of the liquid stream is introduced in the second hydrolysis step.

An amount of 0.202 Kg of solid stream, an amount of 0.121 Kg of liquid stream and an amount of 0.655 kg of water were introduced in a reactor, corresponding to about 9% of dry matter.

An amount of enzyme solution of 100 mg per gram of glucans in the solid stream was added and pH was set to 5 using a KOH solution (2 M). Hydrolysis was performed at 50° C. for a first hydrolysis time of 24 hours and the composition of the first hydrolysis mixture was analyzed at different. At the end of the first hydrolysis time, it was obtained a first hydrolysis stream with a glucose concentration of 34 g/l and a xylose concentration of 10 g/l; the hydrolysis yield reached is of 80% for glucans. Hydrolysis mixture was removed from the reactor and centrifuged in a Thermoscientific centrifuge at 9500 rpm for 10 minutes and separated in a first liquid hydrolyzed portion, comprising the most part of solubilized sugars, and a first solid portion. The first solid fraction was inserted in the reactor for a second hydrolysis step.

An amount of 0.081 Kg of the liquid stream and an amount of 0.437 Kg of water were added to the reactor, corresponding to a dry matter of about 6%. The enzymatic hydrolysis was continued for a second hydrolysis time of 24 hours, at the same conditions of the first hydrolysis step, in the presence of the enzymes recycled in the first solid fraction. No new enzymes were added.

At the end of the second hydrolysis time, it was obtained a second hydrolysis stream with a glucose concentration of 1.8 g/l and a xylose concentration of 3.2 g/l.

Figure 7:
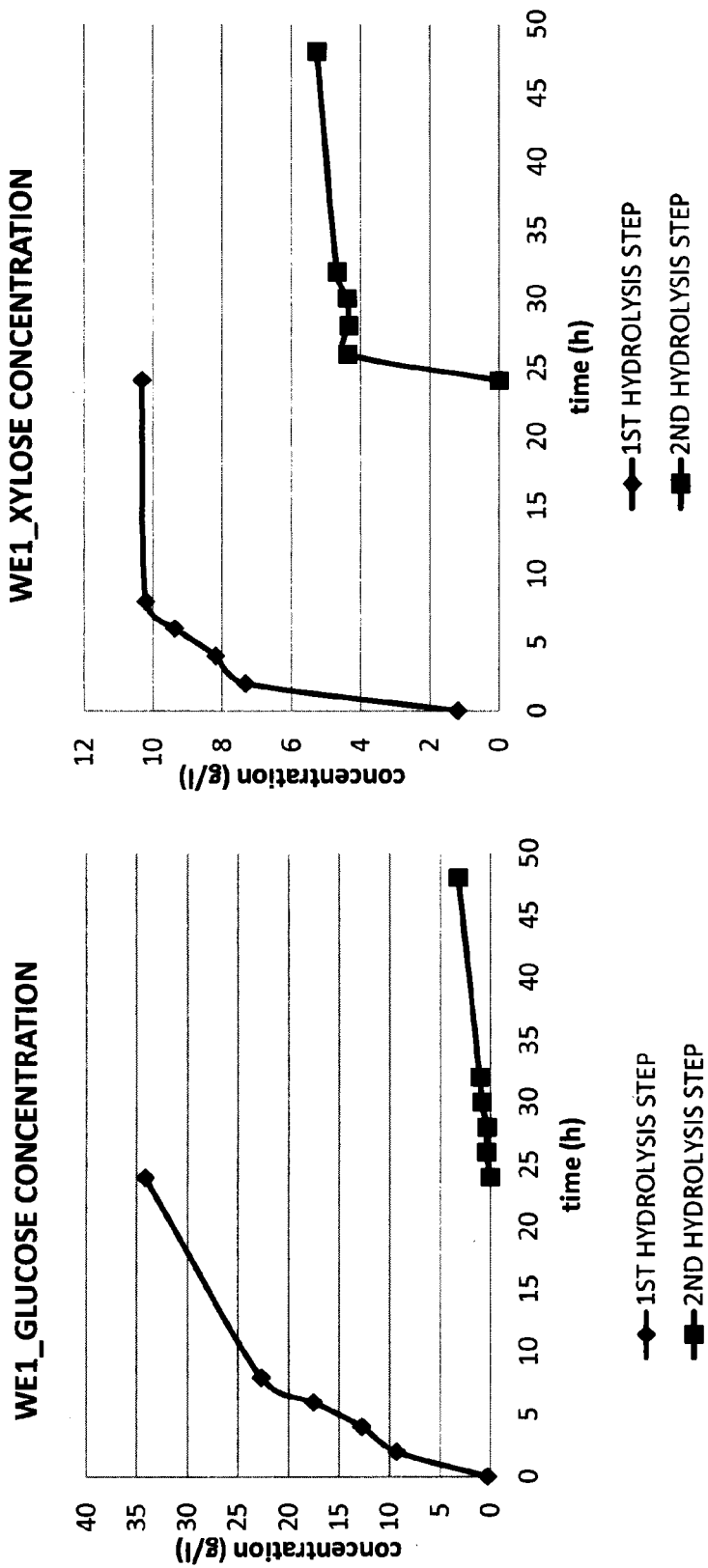
FIG. 7 graphically depicts glucose and xylose concentration in WE1.

FIG. 7 reports the glucose and xylose concentration during the two steps of enzymatic hydrolysis of WE1.

The streams from the two hydrolysis steps were mixed for comparison with CE1. Table 6 reports the composition of the total stream on a dry basis. The global dry matter was 5.7%.

TABLE 6

Composition of the total stream of WE1

| | TOTAL COMPOSITION |
|---|---|
| glucose | 37.6% |
| xylose | 11.5% |
| acetic acid | 1.2% |
| glucoligomers | 1.4% |
| xyloligomers | 2.2% |
| acetyls | 0.2% |
| insoluble glucans | 0.2% |
| insoluble xylans | 0.0% |
| other | 45.8% |

The glucose concentration of the total stream was 36 g/l and the xylose concentration was 14 g/l corresponding to a global hydrolysis yield of 91% of 92% for glucans and xylans respectively.

In WE1, conducted according to the disclosed process, it is obtained a process yield higher than in CE1 and a total stream more concentrated than in CE2. Namely, the amount of water added in the whole hydrolysis is equivalent to that one used in CE1.

We claim:

1. An improved process for the hydrolysis of a pre-treated ligno-cellulosic biomass comprising a solid stream and a liquid stream, said solid stream comprising glucans, xylans and compounds that are not glucans or xylans, said liquid stream comprising xylooligomeres, water and compounds which are not xylooligomers, wherein said process comprises the steps of:
  a) mixing the solid stream and a first portion of the liquid stream;
  b) hydrolyzing at least a portion of the glucans in the solid stream to glucose and at least a portion of the xyloo-ligomers in the first portion of the liquid stream to xylose in the presence of a first hydrolysis catalyst to create a first hydrolysis mixture having a first hydrolysis mixture monomeric sugars concentration and a first hydrolysis mixture hydrolysis catalyst concentration, wherein the first hydrolysis mixture has a first hydrolysis mixture catalyst to monomeric sugars ratio which is the ratio of the weight of the hydrolysis catalyst in the first hydrolysis mixture to the total weight of monomeric sugars in the first hydrolysis mixture; and c) removing at least a portion of the monomeric sugars from the first hydrolysis mixture to create:
  i) a first product stream comprising water, glucose and xylose, wherein said first product stream has a first product stream monomeric sugars concentration, a first product stream catalyst concentration which could be 0 and a first product stream catalyst to monomeric sugars ratio which is the ratio of first product stream catalyst concentration to the first product stream monomeric sugars concentration and
  ii) a partly hydrolyzed stream, which is the first hydrolysis mixture which has had at least a portion of the monomeric sugars removed, wherein the removal of at least a portion of the monomeric sugars from the first hydrolysis mixture occurs while the hydrolysis of at least a portion of the glucans to glucose is still being conducted, and the first hydrolysis mixture catalyst to monomeric sugars ratio is greater than or equal to the first product stream catalyst to monomeric sugars ratio.

2. The process according to claim 1, further comprising the steps of:

d) mixing the partly hydrolyzed stream and a second portion of the liquid stream;

e) hydrolyzing at least a portion of the glucans in the partly hydrolyzed stream to glucose and at least a portion of the xylooligomers in the second portion of the liquid stream to xylose in the presence of a second hydrolysis catalyst comprising at least a portion of the first hydrolysis catalyst to create a second hydrolysis mixture, and f) removing at least a portion of the monomeric sugars from the second hydrolysis mixture to create a second monomeric sugars product stream comprising water, glucose and xylose.

3. The process according to claim 2, wherein the hydrolysis of step b) occurs in a first vessel, and the hydrolysis of step e) occurs in a second vessel.

4. The process according to claim 2, wherein the hydrolysis of step b) and the hydrolysis of step e) occur in the same vessel.

5. The process according to claim 3, wherein the removal of the monomeric sugars from the first hydrolysis mixture and/or the second hydrolysis mixture occurs outside the first vessel.

6. The process according to claim 4, wherein the removal of the monomeric sugars from the first hydrolysis mixture and/or the second hydrolysis mixture occurs outside the first vessel.

7. The process according to claim 1, wherein at least a portion of the partly hydrolyzed stream is purged from the process.

8. The process according to claim 1, wherein at least a portion of the first hydrolysis mixture is purged from the process.

9. The process according to claim 1, wherein at least a portion of the glucans, xylans, and compounds which are not glucans or xylans are purged from the process.

10. The process according to claim 1, wherein the partly hydrolyzed stream has a partly hydrolyzed stream monomeric sugars concentration, and the ratio of the partly hydrolyzed stream monomeric sugars concentration to the first hydrolysis mixture monomeric sugars concentration is less than or equal to 1.0.

11. The process according to claim 1, wherein the hydrolysis comprises enzymatic hydrolysis and the catalyst comprises at least one enzyme capable of hydrolyzing glucans to glucose.

12. The process according to claim 1, wherein the removal of at least a portion of the monomeric sugars from the first hydrolysis mixture is comprised of a process selected from the group consisting of centrifugation, filtration and a combination thereof.

13. The process according to claim 1, wherein the removal of at least a portion of the monomeric sugars from the first hydrolysis mixture and/or the second hydrolysis mixture comprises nano-filtration.

14. The process according to claim 1, wherein the removal of at least a portion of the monomeric sugars from the first hydrolysis mixture and/or the second hydrolysis mixture comprises ultra-filtration.

15. The process according to claim 1, wherein the removal of at least a portion of the monomeric sugars from the first hydrolysis mixture and/or the second hydrolysis mixture comprises centrifugation.

16. The process according to claim 3, wherein the ratio of the mass of the material purged from the process to the mass of the partly hydrolyzed stream introduced into the first vessel or the second vessel is in a range of 5:95 to 50.50.

17. The process according to claim 4, wherein the ratio of the mass of the material purged from the process to the mass of the partly hydrolyzed stream introduced into the first vessel or the second vessel is in a range of 5:95 to 50.50.

18. The process according to claim 1, wherein the ratio on a dry basis of the amount of the pre-treated ligno-cellulosic biomass added to the process to the amount of the first hydrolysis mixture in the process plus the amount of the partly hydrolyzed stream in the process is less than a ratio of 2.1.

19. The process according to claim 3, wherein the pre-treated lignocellulosic biomass is introduced non-continuously into the first vessel.

20. The process according to claim 4, wherein the pre-treated lignocellulosic biomass is introduced non-continuously into the first vessel.

21. The process according to claim 3, wherein the first hydrolysis mixture is removed non-continuously from the first vessel.

22. The process according to claim 4, wherein the first hydrolysis mixture is removed non-continuously from the first vessel.

23. The process according to claim 1, wherein the ratio of the first product stream monomeric sugars concentration to the partly hydrolyzed stream monomeric sugars concentration is greater than 1.0.

24. The process according to claim 1, wherein the first hydrolysis mixture catalyst to monomeric sugars ratio is greater than the first product stream catalyst to monomeric sugars ratio.

25. The process according to claim 1, wherein the first product stream catalyst to monomeric sugars ratio divided by the first hydrolysis mixture catalyst to monomeric sugars ratio is less than a number of 1.0.

26. The process according to claim 1, wherein the ratio of the amount of enzyme expressed in milligrams to the total amount of the beta 1,4 glucans expressed in grams is in a range of 0.5 to 25.

* * * * *